(12) United States Patent
Liedtke

(10) Patent No.: US 6,631,292 B1
(45) Date of Patent: Oct. 7, 2003

(54) BIO-ELECTRICAL IMPEDANCE ANALYZER

(75) Inventor: Rudolph J. Liedtke, Grosse Pointe Park, MI (US)

(73) Assignee: RJL Systems, Inc., Mt. Clemens, MI (US)

( * ) Notice: Subject to any disclaimer, the term of this patent is extended or adjusted under 35 U.S.C. 154(b) by 139 days.

(21) Appl. No.: 09/816,880

(22) Filed: Mar. 23, 2001

(51) Int. Cl.⁷ .................................................. A61B 5/00
(52) U.S. Cl. ....................................................... 600/547
(58) Field of Search ................................ 600/547, 506; 324/713, 600

(56) References Cited

U.S. PATENT DOCUMENTS

| | | | |
|---|---|---|---|
| 3,871,359 A | * | 3/1975 | Pacela .......................... 600/547 |
| 4,911,175 A | | 3/1990 | Shizgal |
| 4,947,862 A | | 8/1990 | Kelly |
| 5,063,937 A | * | 11/1991 | Ezenwa et al. .............. 128/723 |
| 5,086,781 A | | 2/1992 | Bookspan |
| 5,088,489 A | * | 2/1992 | Lerman .......................... 607/7 |
| 5,335,667 A | | 8/1994 | Cha et al. |
| 5,371,469 A | * | 12/1994 | Anderson .................... 324/705 |
| 5,449,000 A | | 9/1995 | Libke et al. |
| 5,503,157 A | | 4/1996 | Sramek |
| 5,615,689 A | | 4/1997 | Kotler |
| 5,749,369 A | | 5/1998 | Rabinovich et al. |
| 5,865,763 A | | 2/1999 | Kotler et al. |
| 6,011,992 A | | 1/2000 | Hubbard et al. |
| 6,339,722 B1 | * | 1/2002 | Heethaar et al. ............. 600/547 |
| 6,442,422 B1 | * | 8/2002 | Duckert ........................ 600/547 |

FOREIGN PATENT DOCUMENTS

| | | | |
|---|---|---|---|
| JP | 63-109841 | * | 5/1988 |
| JP | 4-96733 | * | 3/1992 |
| JP | 2000-245705 | * | 9/2000 |
| JP | 2000-271101 | * | 10/2000 |

| | | | |
|---|---|---|---|
| WO | 8602819 | * | 5/1986 |

OTHER PUBLICATIONS

J.M.H. Risser, et al, *A Comparison of Fat–free Mass Estimates in Men Infected With the Human Immunodeficiency Virus*, Journal of Parenteral and Enteral Nutrition, vol. 19, No. 1, 1995, pp. 28–32.

Michael Ott, et al, *Bioelectrical Impedance Analysis as a Predictor of Survial in Patients with Human Immunodeficiency Virus Infection*, Journal of Acquired Immune Deficiency Syndromes and Human Retrovirology, vol. 9, No. 1, 1995, pp. 20–25.

T.E.M.S. Sluys, et al, Body Composition in Patients With Acquired Immunodeficiency Syndrome: A Validation Study of Bioelectric Impedence Analysis, Journal of Parenteral and Enteral Nutrition, vol. 17, No. 5, 1993, pp 404–406.

R. Liedtke, et al, *Resistance and Capacitance in Biological Conductivity*, RJL Systems, Inc., 1993.

* cited by examiner

Primary Examiner—John A. Jeffery
(74) Attorney, Agent, or Firm—Young & Basile, P.C.

(57) ABSTRACT

An apparatus for measuring the resistance and reactance of a subject, or a segment of a subject, includes a constant current source supplying a periodic high frequency input current to the subject. The constant current source controls the input current to a targeted value by measuring the actual current through the subject and comparing that actual current to the target current. The resulting error signal controls the input current. The input current is supplied to the segment through a coupling transformer, and another coupling transformer coupled to a resistor in the subject path supplies the value of the actual current. The apparatus also includes an impedance measuring circuit that detects an output voltage across the segment, preferably using a detection coupling transformer, and produces at least one of a reactance output signal and a resistance output signal using the output voltage. In one aspect, an automatic shut down circuit is included.

20 Claims, 6 Drawing Sheets

BIO-ELECTRICAL IMPEDANCE ANALYZER

BACKGROUND OF THE INVENTION

1. Field of the Invention

This invention relates in general to a bioelectrical impedance measurement apparatus.

2. Description of the Related Art

Bioelectrical impedance measurements have been employed to determine various body characteristics, such as blood flow, cardiac output and composition including an assessment of body fat, lean body mass and body cell mass. To determine body composition, a four-electrode impedance plethysmograph is usually employed. A first pair of source or current electrodes is connected to a human body typically on a hand and a foot. Specifically, one source electrode is attached to the dorsal surface of a hand over the metacarpals, whereas the other source electrode is attached to the distal end of the third metatarsal bone of the foot. One electrode of a second pair of detecting or sensing electrodes is traditionally attached to the dorsal surface of a hand between the bony prominences of the wrist, whereas a second sensing electrode is positioned between the lateral and medial bony prominence of an ankle. An excitation current generated by the plethysmograph is applied to the source electrodes and thus introduced into the body. For example, an 800 microampere, 50 kHz current is typically employed.

The human body opposes the conduction of electrical current, and this ability to oppose current is called impedance. Impedance is measured by the plethysmograph, which generally includes a measuring circuit, an amplifier and an indicator circuit. Then, the impedance is used to predict other physiological parameters. For example, body resistance can be combined in an equation with the weight and height of the subject to predict total body water (TBW).

Existing measuring devices do not isolate the subject from the electronics of the measuring device to prevent potential electrical shocks and improve the common mode rejection ratio. Further, accuracy of measurement is important because of the use of the measurements as predictors of health. Many of the inaccuracies of the impedance measurements are related to noise generated by the existing measuring circuits themselves. The more noise generated, the less likely small changes in impedance are able to be measured. Temperature sensitivity can also be a problem in existing devices, particularly when the device is portable.

It would be desirable to provide a bioelectrical impedance measurement apparatus that increases the accuracy of a single body compositional measurement of a subject while isolating the subject from the electronic components of the apparatus. It would also be desirable to make the apparatus portable.

SUMMARY OF THE INVENTION

The present invention is an apparatus for determining bioelectrical impedance measurements. Specifically, the present invention is an apparatus for measuring an impedance of a segment of a subject, comprising: a constant current source wherein a level of an input current is controlled by a feedback loop using an error signal representing a difference between an actual current measured through the segment and a target current; and an impedance measuring circuit detecting an output voltage across the segment and adapted to produce at least one of a reactance output signal and a resistance output signal using the output voltage.

In one aspect of the invention, the constant current source comprises: a direct current power supply providing a voltage source to an oscillating current source; a first amplifier connected to the oscillating current source wherein the gain of the first amplifier is controlled by the feedback loop; and an input coupling transformer receiving the output of the first amplifier and adapted to supply the input current through first external leads connectable to the segment. In a preferred aspect, the oscillating current source is a Colpitts oscillator.

In another aspect of the invention, the feedback loop of the constant current source comprises: a reference resistor coupled to a reference coupling transformer for measuring a constant current signal corresponding to the actual current through the segment; means for producing the error signal by comparing the constant current signal to a reference signal corresponding to the target current; and a modulator for controlling the gain of the first amplifier using the error signal. In a preferred aspect, the modulator is an optocoupler that changes resistance based on a value of the error signal.

In another aspect of the invention, the means for producing the error signal comprises: a buffer amplifier connected to the reference transformer and adapted to produce an amplified constant current signal; a rectifier connected to the buffer amplifier and adapted to rectify the amplified constant current signal; and a comparator receiving an output of the rectifier and the reference signal and producing the error signal. The rectifier can be a precision rectifier.

In yet another aspect of the present invention, the impedance measuring circuit comprises: a detection coupling transformer adapted to detect the output voltage; an output amplifier connected to the detection transformer adapted to produce an amplified output signal; and means for converting the amplified output signal into the reactance output signal and the resistance output signal. The amplified output signal can be capacitively coupled to the means for converting the amplified output signal into the reactance output signal and the resistance output signal. Preferably, the detection coupling transformer is designed for a common mode rejection ratio of greater than 90 dB at its operating frequency.

In one aspect of the invention including the means for converting the amplified output signal into the reactance output signal and the resistance output signal, the means includes: an integrator connected to receive the amplified constant current signal; a first balanced synchronous demodulator adapted to produce a first and a second direct current differential signal using a first reference vector provided by the integrator; a second balanced synchronous demodulator adapted to produce a third and a fourth direct current differential signal using a second reference vector provided by the buffer amplifier; a first instrumentation amplifier adapted to convert the first and second direct current differential signals into the reactance output signal; and a second instrumentation amplifier adapted to convert the third and fourth direct current differential signals into the resistance output signal. Preferably, the first and the second balanced synchronous demodulators are two passive analogue phase detectors.

In yet another aspect of the invention, the invention further comprises an automatic shut down circuit adapted to shut down operation of at least one of the constant current source and the impedance measuring circuit after at least one predetermined time period. The automatic shut down circuit can include isolating means to isolate a power supply from at least one of the constant current source and the impedance measuring circuit.

The invention can further comprise reporting means for reporting at least one of the reactance output signal and the resistance output signal.

In one aspect of the invention, the constant current source supplies the input current through first external leads connectable to the segment and the impedance measuring circuit measures the output voltage through second external leads connectable to the segment.

Another aspect of the apparatus for measuring an impedance of a segment of a subject comprises: a constant current source supplying a level of an input current to an input coupling transformer through first external leads connectable to the segment; a detection coupling transformer using second external leads connectable to the segment, which transformer detects an output voltage across the segment; and a circuit adapted to produce at least one output signal using the output voltage.

In one aspect, the invention further comprises a reference resistor coupled to a reference coupling transformer for measuring a constant current signal corresponding to an actual current through the segment and providing an input to the constant current source.

In another aspect of the invention, the level of the input current is controlled by an error signal representing a difference between an actual current measured through the segment and a target current. Preferably, an optocoupler controls the level of the input current using the error signal.

In yet another aspect, the detection coupling transformer is designed for a common mode rejection ratio of greater than 90 dB at its operating frequency.

Thus, the present invention is an apparatus that measures the resistance and reactance of a subject, or portion of a subject, directly while isolating the subject from the electronic components of the apparatus. The invention further provides a very accurate body composition measurement due to low noise. The extremely low power consumption of the apparatus and its relative temperature insensitivity contribute to its easy portability.

BRIEF DESCRIPTION OF THE DRAWINGS

The various features, advantageous and other uses of the present invention will become more apparent by referring to the following detailed description and drawings in which.

DETAILED DESCRIPTION

Referring now to FIGS. 1–5B of the drawings, there is depicted an apparatus for measuring the impedance of biological tissue and fluids of a subject, or portion of a subject, while isolating the subject from the electronic components of the measuring circuit. The apparatus 10 delivers a constant current to the subject using a constant current system, to be hereinafter described, measures the voltage drop across the subject, determines the resistance and reactance internal to the subject from the voltage drop and reports the result.

Figure 1:
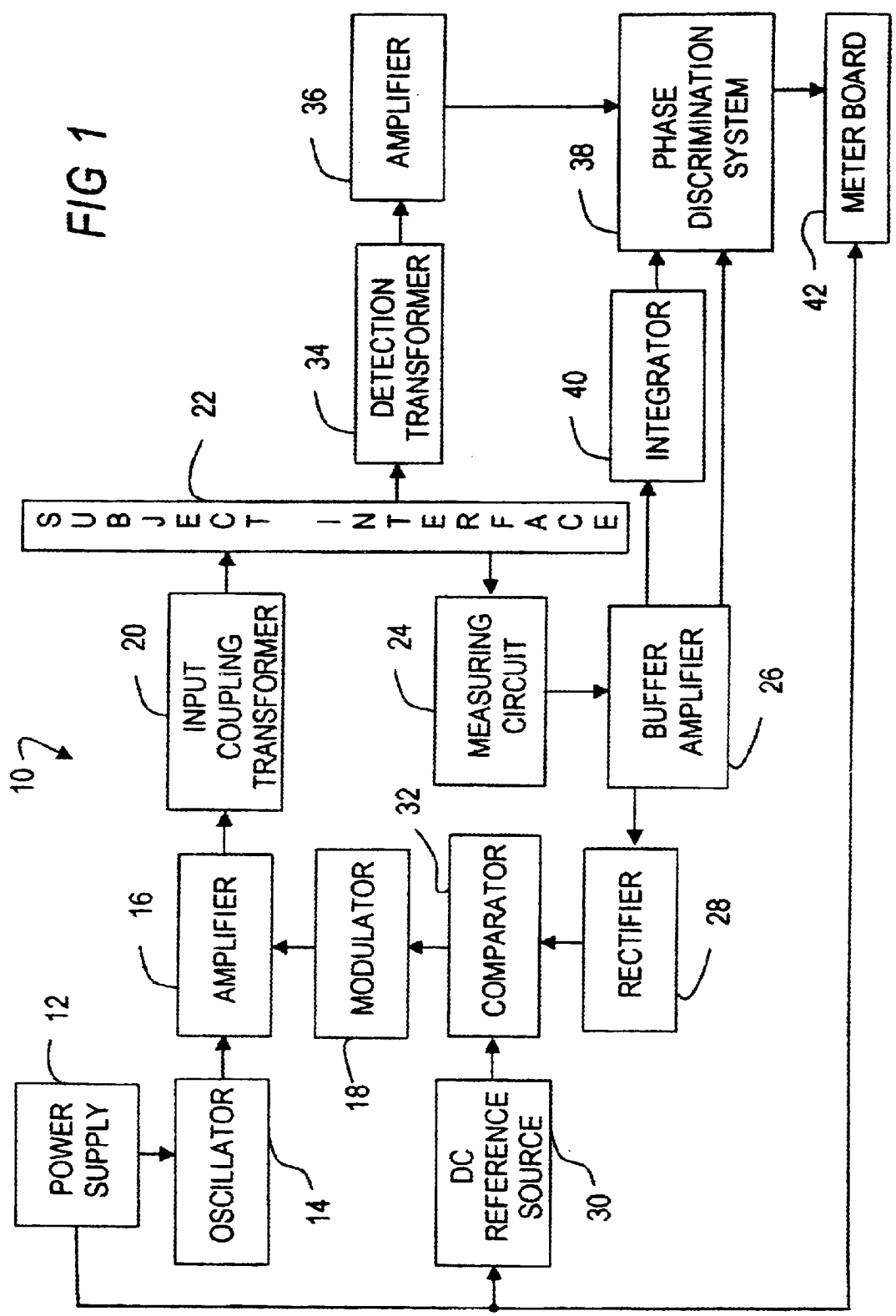
FIG. 1 is a functional block diagram of one aspect of a device according to the present invention.

The apparatus 10, shown generally in FIG. 1, is controlled by a power supply 12, to be described in further detail hereinafter, which power supply 12 preferably includes a single nine-volt alkaline battery. The power supply 12 provides DC operating voltages for the system of $V_{ss}+$ and $V_{dd}-$. The power supply also provides a precision DC source for analog processing of +DC volts and −DC volts. In one aspect, $V_{ss}+$ and +DC volts are each +5.0 volts, and $V_{dd}-$ and −DC volts are each −5.0 volts. The constant current system is a system that causes current in the subject to remain constant at a predetermined value, preferably 425 microamps at 50 kHz. The maximum current should not exceed 500 microamps RMS at 50 kHz. To maintain a constant current, the constant current system supplies an input current to the subject, compares the current through the subject to a reference, and adjusts the input current based on the comparison. In a preferred aspect, the constant current system is a transformer coupled, open loop DC servo system that includes an oscillator 14, an amplifier 16, a modulator 18, an input coupling transformer 20, a measuring circuit 24, a buffer amplifier 26, a rectifier 28, a DC reference source 30, and a comparator 32.

Specifically, an oscillator 14 provides a main oscillating signal to drive an amplifier 16. As shown in detail in FIG. 2, the amplifier 16 is preferably configured as a non-inverting operational amplifier ("op amp"), i.e., the sinusoidal output of the oscillator 14 is input into the non-inverting input of the op amp, and the feedback of the op amp is coupled to the inverting input through a resistor. Amplifier 16 and all of the other op amps in the apparatus 10, unless stated otherwise, are standard op amps such as op amps OP282 and OP482 from Analog Devices of Norwood, Mass. The gain of the amplifier 16, and thus the current through the subject, is controlled by a modulator 18, to be described in further detail hereinafter.

Figure 2:
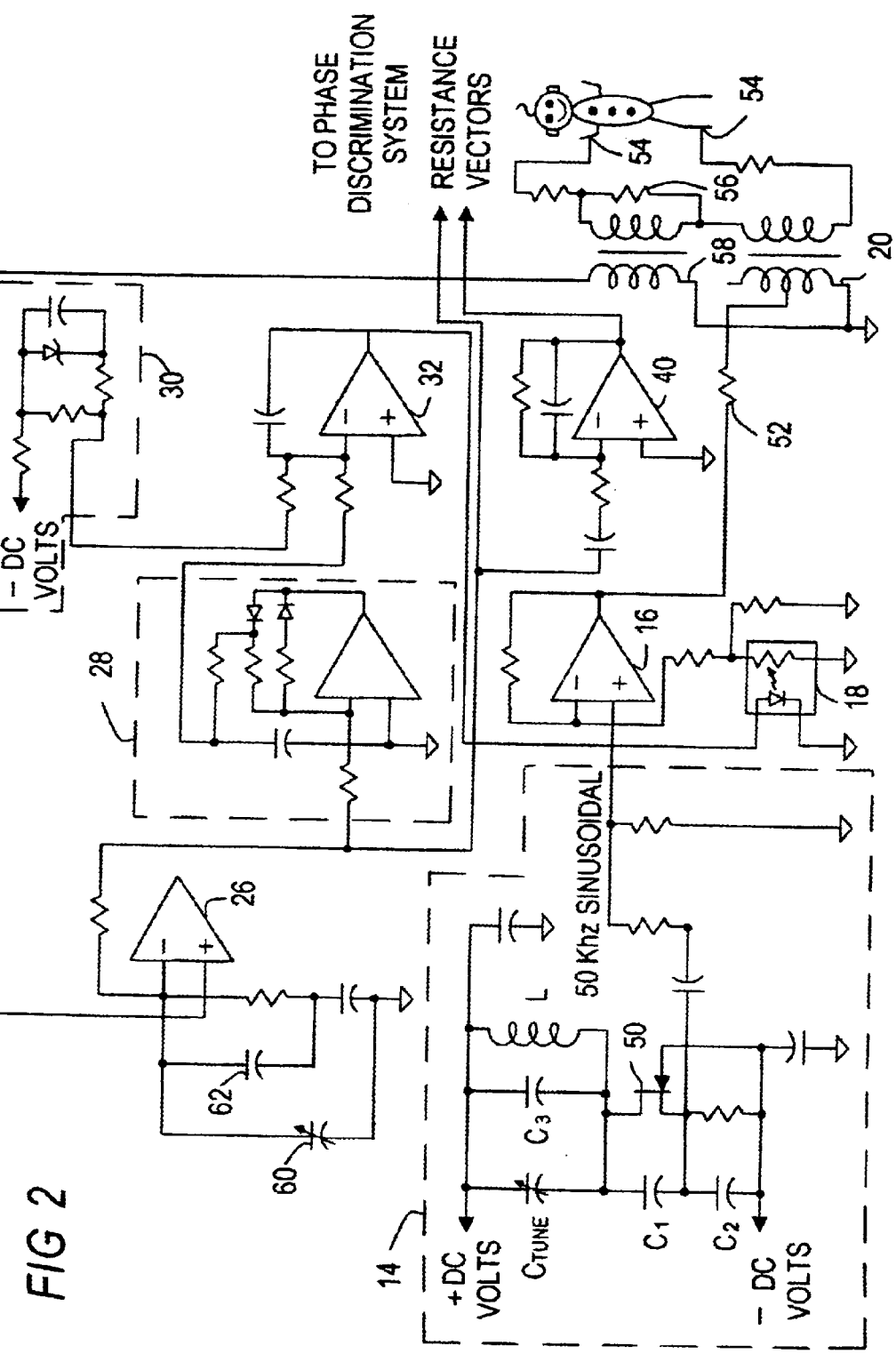
FIG. 2 is a schematic of a 50 kHz oscillating and constant current source of the present invention.

The oscillator 14 is also shown in detail in FIG. 2. Preferably, the oscillator 14 is a single FET transistor configured as a Colpitts oscillator, which creates an extremely clean sinusoidal wave with low power drain. Although the invention is described in reference to a Colpitts oscillator, any oscillator can be incorporated into the present invention. The oscillator 14 is supplied by a DC voltage source, preferably +DC volts and −DC volts from the power supply 12. Resonance is achieved by an inductive tank circuit with two series capacitors. The frequency of oscillation is described by the following equation:

$$f_o = \frac{1}{2*\pi*(LC_{Total}^2)^{\frac{1}{2}}}; \text{ where}$$

$$C_{Total} = C_{Tune} + \frac{C_1 * C_2}{C_1 + C_2}; \text{ and where}$$

$f_o$ is the frequency of oscillation;

L is the inductor of the tank circuit and is preferably 8.2 Mhy;

$C_1$ and $C_2$ are the two series capacitors of the tank circuit and are preferably each 2200 pf capacitors; and $C_{Tune}$ is a tuning capacitor rated from 15 to 60 pf.

Capacitor $C_3$ is in parallel to $C_{Tune}$, and is preferably a selected 50–390 pf capacitor. Together, $C_3$ and $C_{Tune}$ tune the frequency of oscillation. All of the capacitors in the oscillator 14 are preferably silver mica capacitors because of their zero temperature coefficient. The field-effect transistor (FET) Colpitts oscillator is biased for zero DC drift, that is, the gate is grounded. For this reason, this oscillator 14 displays superior performance with respect to frequency drift and temperature. A suitable FET 50 is the 2N4416A n-channel junction FET by Siliconix Inc. of Santa Clara, Calif. The center tap of $C_1$ and $C_2$ is connected to the source of the FET 50, thereby creating a negative feedback path where the gain is slightly greater than one. The oscillator gain at this point will diverge or converge to create a precise sinusoidal wave, preferably at 50 kHz. The base output impedance is approximately 1400 ohms at resonance. The oscillator 14 can incorporate a conventional attenuator for the sinusoidal signal prior to its input into the amplifier 16.

Also shown in FIG. 2, the output of the amplifier 16 drives a constant current input coupling transformer 20, preferably through a series limiting resistor 52 of 1.0 kilo-ohm. The input coupling transformer 20 supplies a current to the subject through conventionally placed electrodes 54 in the subject interface 22 through two buffer resistors. The electrodes 54 could be either standard electrodes or two electrodes from a tetrapolar lead, with the additional two electrodes detecting the voltage drop caused by the subject impedance as hereinafter described. The input coupling transformer 20 is a 600 ohm one-to-two transformer, by example, where the primary is grounded, but the secondary is not.

The actual current flowing through the subject is measured in the subject interface 22 by a measuring circuit 24, shown in FIG. 1. Returning now to FIG. 2, the measuring circuit 24 includes a constant current reference resistor 56, preferably 1.0 kilo-ohm, placed in the subject constant current path and coupled back to the remainder of the constant current system with a one-to-one reference coupling transformer 58, as shown in FIG. 2. The reference coupling transformer 58 is a 600 ohm one-to-one transformer, by example, where the primary is ungrounded, but the secondary is grounded. Both the input coupling transformer 20 and the reference coupling transformer 58 should have an appropriate isolation barrier, such as a 750 volt RMS isolation barrier. This configuration, together with the configuration of the detection transformer 34 as hereinafter described, isolates the subject from all active circuitry.

The secondary of the reference coupling transformer 58 is input into the non-inverting input of a buffer amplifier 26 with a gain of preferably 6.5. As shown in detail in FIG. 2, the buffer amplifier 26 is a standard non-inverting op amp in one aspect of the invention. The inverting input of the buffer amplifier 26 is grounded through a resistor in series with a capacitor. The buffer amplifier 26 incorporates an adjustable capacitor 60 in parallel with both the resistor and the capacitor and a selected capacitor 62 in parallel with the resistor. Together, the adjustable capacitor 60 and the selected capacitor 62 adjust the vector of the full scale resistance reported by the meter board 42, to be discussed in more detail hereinafter. The value of the selected capacitor 62 depends upon the reference coupling transformer 58 and is a 150 to 200 pf mica capacitor, for example. The adjustable capacitor 60 varies from 15–60 pf in this aspect. The output of this buffer amplifier 26, is fed through a resistor and provides reference vectors for the phase discrimination system 38, shown in FIG. 1 and also to be discussed in more detail hereinafter.

Returning now to FIG. 1, the output of the buffer amplifier 26, which is an indicator of the actual current flowing through the subject, is also used to derive a DC error signal used to control the modulator 18, which in turn controls the current through the subject to a predetermined value by controlling the gain of the amplifier 16. In a preferred aspect, the modulator 18, shown in FIG. 2, is an optocoupler consisting of a light emitting diode (LED) optically coupled to a photocell. The photocell is a sealed cadmium sulfide (CdS) resistive conductor that changes resistance by light intensity from the LED. As to be discussed in further detail hereinafter, the DC error signal is supplied to the anode of the LED, while the cathode is grounded. The photocell resistance is high when the LED current is "off" and low when the LED current is "on." The resistive conductor is grounded on one end and placed in parallel with a resistor. The two elements are connected to the inverting input of the amplifier 16 through another resistor. A suitable optocoupler is NSL-28 or NSL-28AA by Silonex, Inc. of Montreal, Quebec, Canada. Although the modulator 18 could take the form of an FET, or some other device, an optocoupler is preferred because its use results in very little phase shift. Further, use of an optocoupler minimizes the required gain of the amplifier 16.

As shown generally in FIG. 1, the output of the buffer amplifier 26 is rectified through a rectifier 28, producing a rectified voltage representing the actual current. The rectified voltage is compared in a comparator 32 to a DC reference representing the desired current level. The DC reference is generated by a DC reference source 30. The comparator 32 produces the DC error signal that drives the modulator 18. This DC error signal is a voltage that represents the difference between the actual current in the subject and the desired current.

Turning to FIG. 2, more details of the rectifier 28, comparator 32 and DC reference source 30 are shown. While the rectifier 28 can be a standard rectifier, in a preferred aspect the rectifier 28 is a precision rectifier including a resistor array coupled to an op amp. Specifically, the output of the buffer amplifier 26 is supplied to one input of an op amp through an input resistor, along with feedback from parallel diodes arranged such that the forward conduction of each is switch with reference to the feedback path. Each diode is in series with a resistor, each resistor located closest to the input. Another resistor taps the point between the cathode of the diode with forward conduction with reference to the feedback path and its series resistor. The other end of this resistor is connected through a capacitor to the other input of the op amp and is then grounded. The output from this resistor is also the rectified voltage representing the actual current that is supplied to the comparator 32. All of the resistors incorporated into the rectifier 28 are the same value, 4.7 kilo-ohms by example.

The DC reference source 30 should produce a very steady, fixed DC reference, preferably accomplished using a precision shunt regulator diode. In the aspect shown in FIG. 2, the DC reference source 30 is supplied by a negative voltage source, such as −DC volts from the power supply 12, which goes through a voltage divider in parallel with a LM336-2.5 reference diode by National Semiconductor Corp. of Santa Clara, Calif. Specifically, the negative voltage source −DC volts is fed through a resistor is connected to the anode of the reference diode. Prior to this connection to the anode of the reference diode, another resistor is connected such that the second end of the resistor is connected to the cathode of the reference diode through another resistor. A capacitor is placed in parallel to the reference diode. This configuration results in a precision DC reference of 1.0 volt, for example, at the second end of the resistor. In an alternative design, a standard zener diode could be incorporated in place of the shunt regulator diode.

The comparator 32 is a standard comparator that compares the rectified signal from the rectifier 28 to the DC reference from the DC reference source 30. The comparator 32 shown in FIG. 2 has a grounded non-inverting input. The precision rectified signal and the precision DC reference are supplied through resistors of the same value, 100 kilo-ohms by example, to the inverting input through a summing point, which point also includes the feedback supplied through a capacitor. As mentioned, the output of the comparator 32 is the DC error signal that drives the modulator 18.

Figure 3:
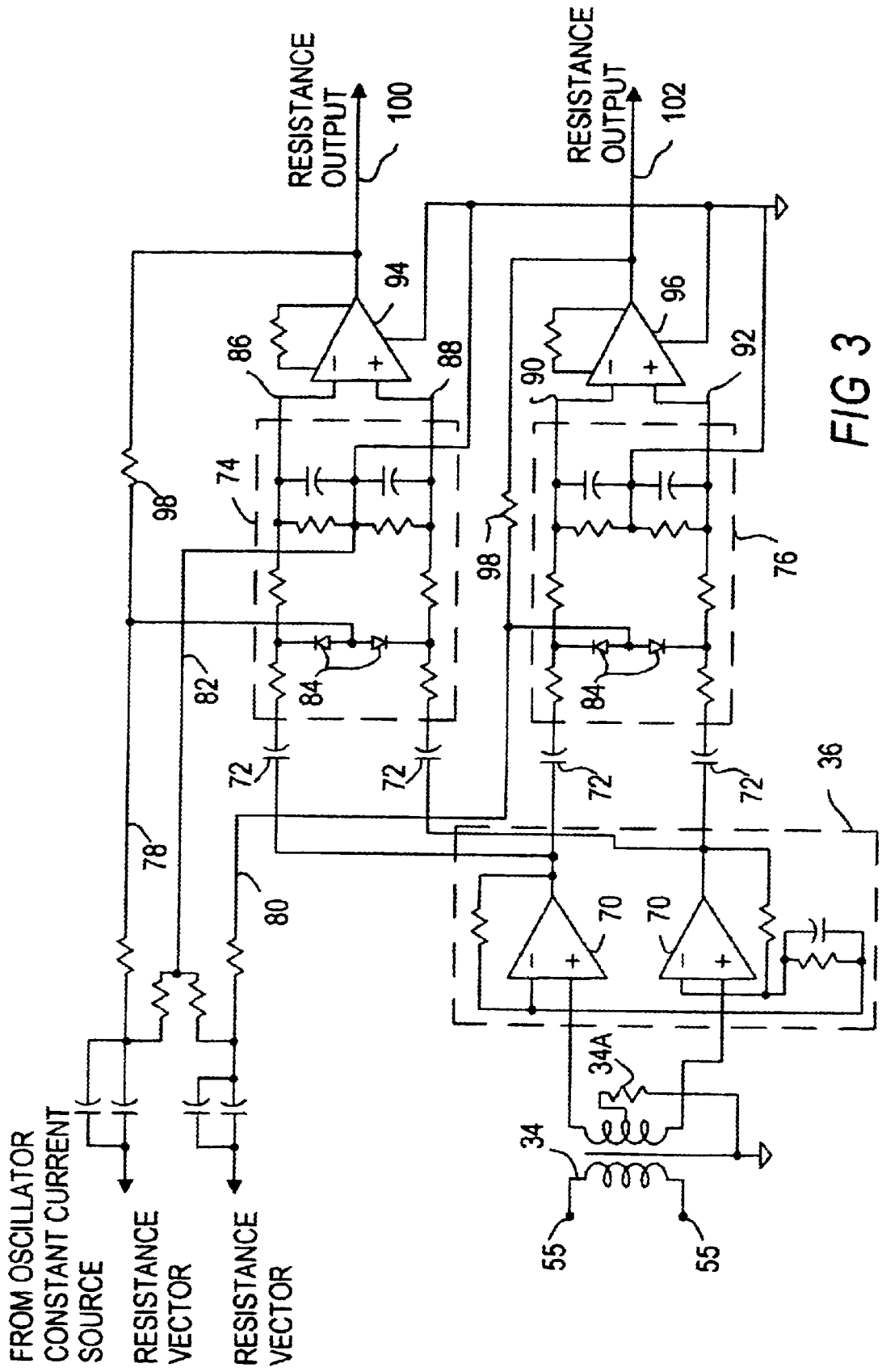
FIG. 3 is a schematic of a passive detector and phase discriminator of the present invention.

Returning now to FIG. 1, the detection of a voltage drop across the subject, and thus the first step in the measurement of the impedance, is performed by a detection transformer 34 through conventionally placing standard electrodes 55 in the subject interface 22 close to the leads 54, which leads 54 are shown in FIG. 2. Alternatively, the two electrodes 55 could be part of a tetrapolar lead, as previously discussed. The detection transformer 34 receives the unbalanced input from the subject at its primary and provides a balanced output at its secondary. Preferably, the detection transformer 34 is a custom-wound transformer with a turns ratio of 10,000 to 1, and an operating frequency of 50 kHz. The detection transformer 34 is heavily insulated to reduce capacitance between the layers and is designed for a common mode rejection ratio of greater than 90 DB with virtually zero insertion loss, that is, the insertion loss is greater than 1.0 mega-ohm impedance at the operating frequency. In a high pot test, the sustainable voltage greater than 1000 volts AC. As shown in FIG. 3, this transformer 34 provides no reference to ground in the subject, and the secondary is grounded through a center-tapped resistor 34a, preferably 1.0 mega-ohm.

The voltage from the secondary of the detection transformer 34 is amplified through an RF amplifier 36, shown generally in FIG. 1. In the aspect shown in detail in FIG. 3, the RF amplifier 36 consists of two op amps 70 configured as non-inverting common mode instrumentation amplifiers. Specifically, each tap from the secondary of the detection transformer 34 is connected to a non-inverting input of one of the op amps 70. The inverting inputs of the op amps 70 receive feedback through resistors, and the inverting inputs are coupled through another resistor in parallel with a capacitor, which controls the common mode gain. The subject variable differential outputs of the RF amplifier 36 are capacitively coupled to the phase discrimination system 38 through four coupling capacitors 72 of 0.1 micro-farads each, by example.

As also shown in FIG. 3, the phase discrimination system 38 includes phase detectors 74, 76. Each phase detector 74, 76 is an identically designed balanced synchronous demodulator, except for the analog reference signal supplied to each. In the aspect shown, the phase detectors 74, 76 are two passive analogue phase detectors that resolve the subject reactance and resistance obtained from the RF amplifier 36 through comparison to analog reference reactance 78 and resistance 80 signals. The output of each op amp 70 of the RF amplifier 36 provides one input to each phase detector 74, 76. Although the phase detectors shown are passive analogue detectors, in an alternative aspect, the invention can incorporate digital demodulators. However, the solid state demodulator is preferred for low power consumption and overall temperature stability due to the excellent temperature match of the demodulation diodes 84, to be discussed herein.

As discussed previously with regards to FIG. 2, the output of the buffer amplifier 26 is fed through a resistor and provides reference vectors for the phase discrimination system 38. Specifically, the buffer amplifier 26 provides a reference resistance vector and supplies an input into an integrator 40. The integrator 40 can be any standard device providing a 90 degree phase-shifted vector using the output of the buffer amplifier 26. One integrator 40 incorporating a standard op amp is shown in detail in FIG. 2. The non-inverting input of the op amp is grounded, while the signal from the buffer amplifier is fed through a series resistor and capacitor connected to the inverting input of the op amp. The feedback of the op amp includes another capacitor in parallel with another resistor, and the feedback is coupled to the inverting input. The output of the integrator 40 is a reference reactance vector.

Returning now to FIG. 3, the reference reactance and resistance vectors supplied by the integrator 40 and the buffer amplifier 26, respectively, are each fed through two capacitors of the same value arranged in parallel. The resulting analog reference reactance 78 and resistance 80 signals are supplied to the phase detectors 74 and 76, respectively. The signals 78, 80 are also fed through resistors of the same value to a common ground 82, which is also supplied to both phase detectors 74, 76.

In general, the phase detectors 74, 76 each include circuitry for demodulation and low pass filtering. The phase detectors 74, 76 include two series resistors coupled to the coupling capacitors 72. Phase demodulation is achieved by switching the forward conduction of two demodulation diodes 84 with respect to each reference signal. Specifically, between the two series resistors in each leg of each phase detector 74, 76 is a center tap connected to the cathode of a demodulation diode 84. The analog reference analog reference reactance 78 and resistance 80 signals are each supplied to the common anodes of the demodulation diodes 84. After the second series resistor of each leg of the phase detector 74, 76, two resistors are placed in parallel with two capacitors. The center tap between each resistor and capacitor is grounded to the common ground 82. Preferably, the diodes 84 are those on the CA3039 diode array from Harris Semiconductor (Intersil Corporation) of Palm Bay, Fla. because the temperature match between the diodes is typically 1 micro-volt per degree Celsius, resulting in temperature stability.

The signals produced after demodulation and low pass filtering through the phase detectors 74, 76 are two DC differential signals 86, 88 referenced to ground representing the reactance amplitude and two DC differential signals 90, 92 referenced to ground representing the resistance amplitude. These signals 86, 88, 90 and 92 are then converted to single-ended DC outputs 100, 102 by a pair of high quality instrumentation amplifiers 94, 96. The reactance differential signals 86 and 88 are input into the inverting and non-inverting inputs, respectively, of the first amplifier 94, and the output of first amplifier 94 is the reactance DC output 100. The resistance differential signals 90 and 92 are input into the inverting and non-inverting inputs, respectively, of the second amplifier 96, and the output of the second amplifier 96 is the resistance DC output 102. An external resistor is connected to each amplifier 94, 96 such that the gain of each is 3.00 +/– one percent. The DC output 100, 102 of each instrumentation amplifier 94, 96 is coupled to its respective analog reference signal 78, 80 through an optional resistor 98, which performs the function of boosting the linearity of the signal. The instrumentation amplifiers 94, 96 should have low DC offset and excellent temperature stability. One suitable amplifier is AD623 from Analog Devices of Norwood, Mass.

Figure 4:
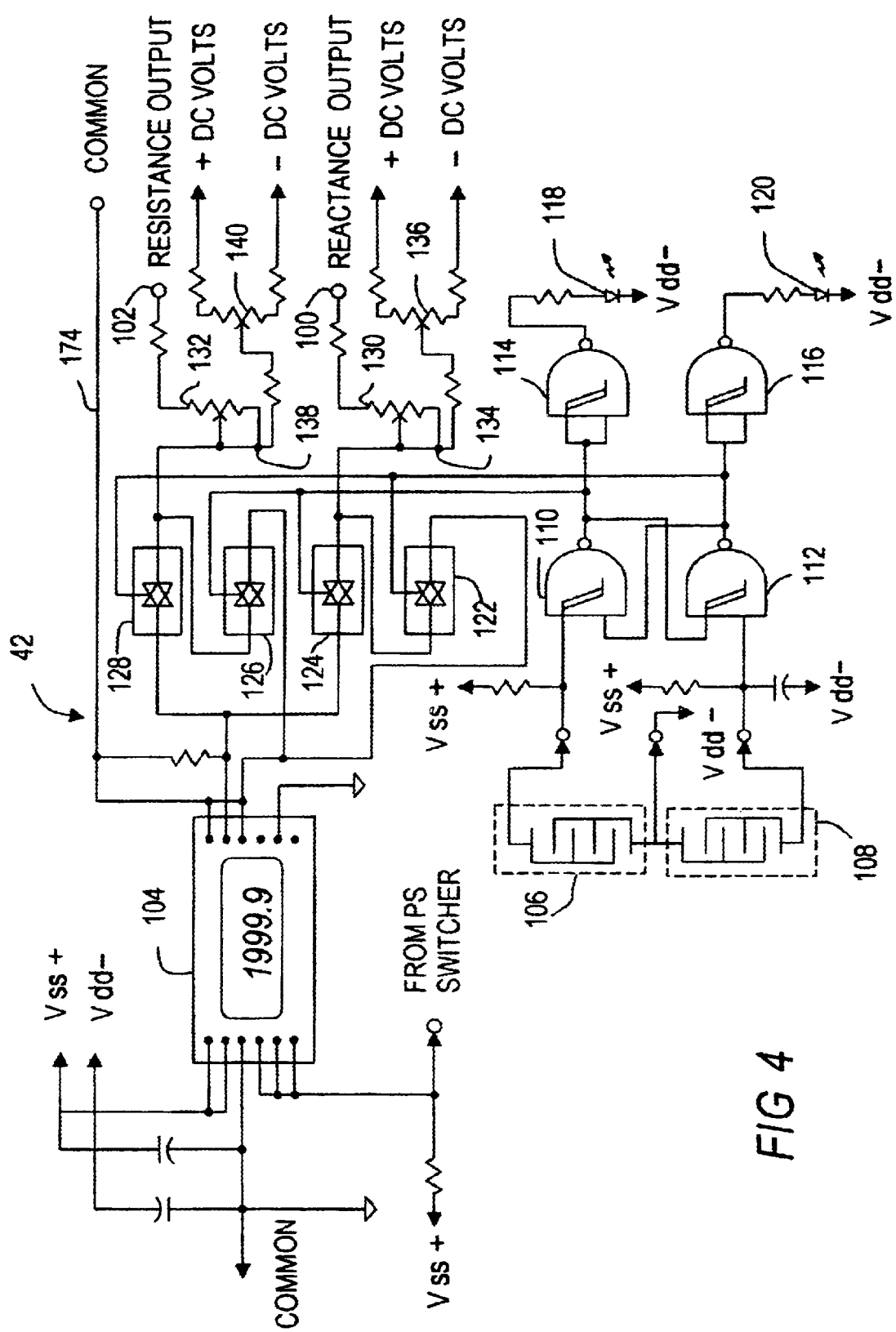
FIG. 4 is a schematic of a meter board according to one aspect of the present invention.

The resulting DC voltage outputs 100, 102 from the instrumentation amplifiers 94, 96 are supplied to the meter PC board 42, shown generally in FIG. 1 and in detail in FIG. 4. The reactance 100 and resistance 102 DC outputs could be, for example, voltage signals between zero and four volts, where four volts equals 2000 ohms. As shown in FIG. 4, the DC outputs 100, 102 are supplied to a display digital panel meter 104 via a resistance-reactance CMOS analogue selection multiplexer. One suitable digital panel meter 104 is the DMS40LCD-0/1-5 digital panel voltmeter from Datel, Inc. of Mansfield, Mass. The digital panel meter 104 is conventionally supplied by the DC voltages $V_{ss}+$ and $V_{dd}-$ and the power supply common 174, shown in FIG. 5B and to be discussed hereinafter. One pin of the digital panel meter 104 of FIG. 4 is grounded, while another is connected to the power supply switcher 176, shown in FIG. 5B and to be discussed hereinafter.

Returning now to FIG. 4, the reactance selector 106 and the resistance selector 108 switch the display on the digital panel meter 104 from resistance to reactance and back. The selectors 92 can be any type of switch such as touch pads, for example. The selectors 106, 108 are commonly connected to $V_{dd}-$. When either selector 106 or 108 is pressed, a circuit is completed, providing input signals to two 2-input NAND gates 110 and 112 with Schmitt-trigger action on both inputs (NAND Schmitt trigger), arranged in a flip-flop configuration. Between selector 106 and trigger 110 is a tap where $V_{ss}+$ is connected through a resistive load. Between selector 108 and trigger 112 is a tap where $V_{ss}+$ is connected through a resistor and $V_{dd}-$ is connected through a capacitor.

The output from the NAND Schmitt trigger 110 provides both inputs to another NAND Schmitt trigger 114. The output of the trigger 114 is connected to a resistor connected to the anode of an LED 118. The cathode of the LED 118 is connected to a negative DC voltage $V_{dd}-$. When the selector 106 is pressed, LED 118 provides a visible indicator that the digital panel meter 104 is reporting the resistance through the subject. Similarly, the output from the NAND Schmitt trigger 112 provides both inputs to another NAND Schmitt trigger 116. The output of the trigger 116 is connected to a resistor connected to the anode of an LED 120. The cathode of the LED 120 is connected to a negative DC voltage $V_{dd}-$. When the selector 108 is pressed, LED 120 provides a visible indicator that the digital panel meter 104 is reporting the reactance through the subject. The NAND Schmitt triggers 110, 112, 114, 116, and all of the triggers in the apparatus 10, can be provided by any standard chip. One suitable quad 2-input NAND Schmitt trigger chip is CD4093BCN from National Semiconductor of Santa Clara, Calif. Another is MC14093B by ON Semiconductor of Phoenix, Ariz.

In addition to providing inputs to the triggers 114, 116 controlling the operation of the LEDs 118, 120, the outputs of the triggers 110, 112 provide control signals to four bilateral switches 122, 124, 126, 128, such as those contained on the quad analog switch/quad multiplexer MC 14066B by ON Semiconductor of Phoenix, Ariz. Specifically, the output of the trigger provides the control signal for the second switch 124 and the third switch 126, while the output of the trigger 112 provides the control signal for the first switch 122 and the fourth switch 128. The control signals of the switches 122, 124, 126, 128 determine whether the reactance DC output 100 or the resistance DC output 102 is displayed on the digital panel meter 104.

While common mode rejection is intrinsic throughout the entire design, requiring no common mode adjustments, zero and full scale resistance and reactance must be adjusted to receive accurate values for the resistance and reactance of the subject at the digital panel meter 104. In the aspect shown in FIG. 4, a first 10k trim potentiometer 130 in series with a resistor receiving the reactance DC output 100 from the instrumentation amplifier 94 adjusts the reactance zero. The first 10k potentiometer 130 connects to a point 134, where a resistor is connected to a first 1.0k trim potentiometer 136, the potentiometer 136 in series with a resistor connected to +DC volts and a resistor connected to −DC volts. A second 10k trim potentiometer 132 in series with a resistor receiving the resistance DC output 102 from the instrumentation amplifier 96 adjusts the resistance zero. The second 10k trim potentiometer 132 connects to a point 138, where a resistor is connected to a second 1.0k trim potentiometer 140, the potentiometer 140 in series with a resistor connected to +DC volts and a resistor connected to −DC volts. Full scale resistance and reactance are adjusted by the first and second 1.0k trim potentiometers 136 and 140, respectively, in conjunction with the selected capacitor 62 and the adjustable capacitor 60 of the buffer amplifier 26, described previously and shown in FIGS. 1 and 2.

Returning now to FIG. 4, the reactance DC output 100 is supplied to the inputs of the first switch 122 and second switch 124 through the point 134. The outputs of the first switch 122 and the second switch 124 are analog inputs provided to the appropriate pin of the digital panel meter 104. The resistance DC output 102 is supplied to the inputs of the third switch 126 and the fourth switch 128 though the point 138. The outputs of the third switch 126 and the fourth switch 128 are analog inputs coupled to the outputs of the first switch 122 and second switch 124, respectively, and are thus provided to the appropriate pin of the digital panel meter 104. Prior to its input into the digital panel meter 104, the analog input from the output of the first switch 122 and the third switch 126 is connected to the power supply common 174, shown in FIG. 5B. As shown in FIG. 4, prior to its input into the digital panel meter 104, the analog input from the output of the second switch 124 and the fourth switch 128 is connected to the power supply common 174, shown in FIG. 5B, through a resistor.

Figure 5A:
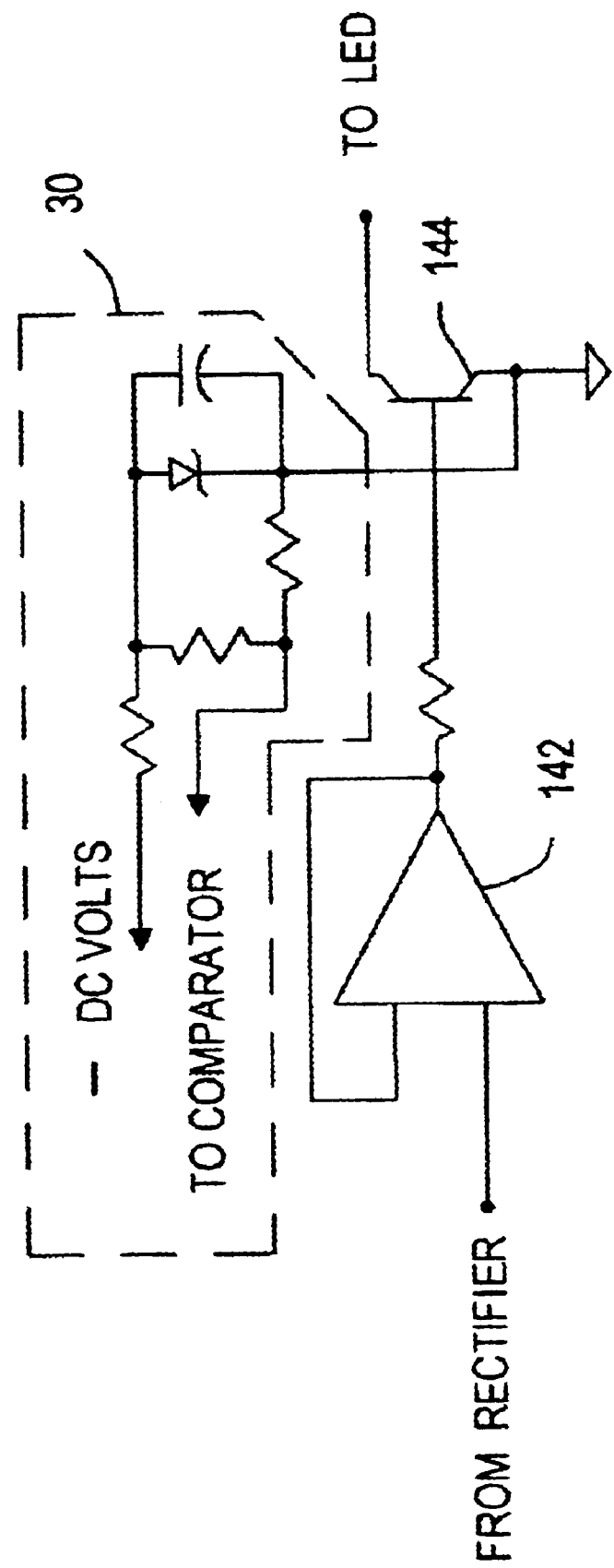
FIG. 5A is a partial schematic showing the connection of a shut-down circuit according to one aspect of the present invention.

In one aspect of the invention, an auto shut-down circuit cuts off the power to most components of the apparatus 10 under predetermined conditions. As shown in FIG. 5A, an op amp 142 amplifies the precision absolute value generated by the rectifier 28. That signal is supplied to the base of a transistor 144 through a resistor, and the emitter is connected to the common cathode, capacitor and resistor connection of the DC reference source 30. The collector of the transistor 144 is supplied to an optocoupler 150, shown in FIG. 5B, which optocoupler 150 includes an LED on the input side and a MOSFET on the output side. A suitable optocoupler is NEC's PS7141-1A, available from California Eastern Laboratories of Santa Clara, Calif. or HSSR-8400 from Agilent Technologies of Palo Alto, Calif. The optocoupler 150 provides an input to the programmable timer 156, to be hereinafter discussed, which determines, in part, how long the apparatus 10 operates prior to shut down. The optocoupler 150 also isolates the battery 170, to be hereinafter discussed, from the remainder of the power supply 12, so that only the timer 156 and some related components are receiving power at all times.

Figure 5B:
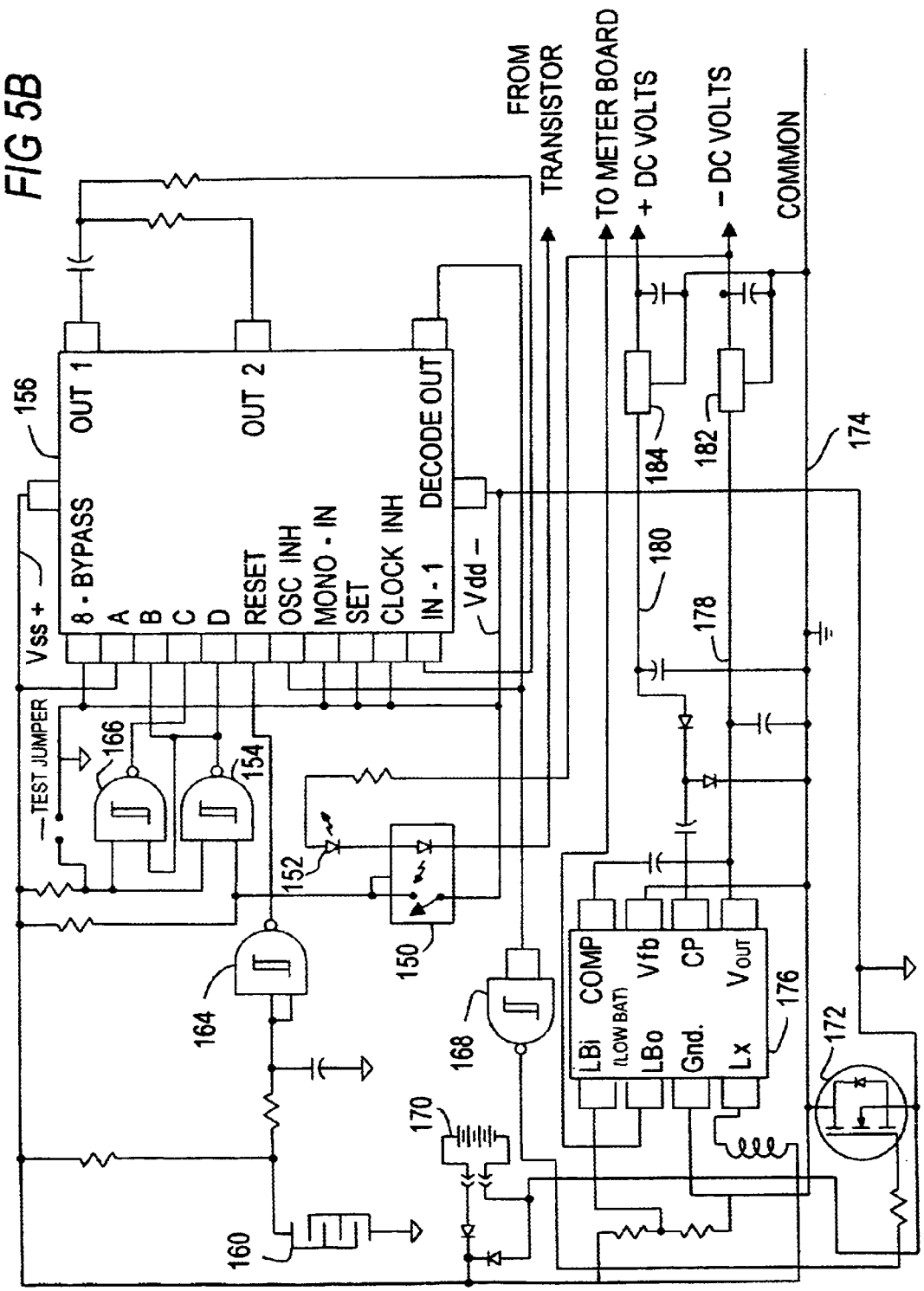
FIG. 5B is a partial schematic of the shut-down circuit and a schematic of the voltage supply according to one aspect of the present invention.

Turning now to FIG. 5B, the collector of the transistor 144 is supplied to the LED cathode of the optocoupler 150. The LED anode of the optocoupler 150 is connected to the cathode of another LED 152, and the anode of the LED 152 is connected to +DC volts through a series resistor. The MOSFET drain of the optocoupler 150 is connected to one input of a 2-input NAND Schmitt trigger 154. The other input to the trigger 154 will be described hereinafter. The MOSFET source is connected to the negative supply voltage $V_{dd}-$, which provides a low voltage input to a programmable timer 156.

As shown in FIG. 5B, the programmable timer 156 is a multiple stage ripple counter capable of achieving a variety of timing based on different conditions. The programmable timer 156 shown is MC14536B from ON Semiconductor of Phoenix, Ariz. Another suitable chip is HCF4536BE by STMicroelectronics of Geneva, Switzerland. The programmable timer 156 would start counting upon a signal to its Reset input, and time out based on the system conditions as indicated by the input signals into the timer 156. For example, the timer 156 would allow operation of the apparatus 10 for 9.42 seconds when no subject is connected to the leads and 10.05 minutes when a subject is connected to the leads, as indicated by the output of the optocoupler 150. The programmable timer 156 should also be capable of operating for a longer period of time for a test mode, such as 160.79 minutes.

The timer 156 Reset input is triggered by an "ON" switch 160 provided with a connection to ground. The "ON" switch 160 can be any suitable switch, such as a touch pad. The other end of the switch 160 is connected to the positive supply voltage $V_{ss}+$, which provides a high voltage input to the programmable timer 156 through a resistor before the switch is connected to a series resistor connected to a grounded capacitor. Then, the connection from the "ON" switch 160 is provided to both inputs of a NAND Schmitt trigger 164. The output of the trigger 164 provides the Reset input to the timer 156.

As mentioned, the timer 156 times out based on the system conditions as indicated by the inputs to the timer 156. One input to the timer 156 is the Reset, at a high level when the "ON" switch 160 is pressed. Another input, also previously mentioned, is the output of the 2-input NAND Schmitt trigger 154, which receives as one of its inputs the output of the MOSFET drain of the optocoupler 150. The output of the trigger 154 provides inputs to two pins B, D of the timer 156, where pins B and D are inputs that together with pins A and C, select the flip-flop stage to be connected to the Decode Out. The output of the trigger 154 also supplies an input to another 2-input NAND Schmitt trigger 166. The second input of each trigger 154 and 166 are coupled and connected to $V_{ss}+$ through a resistor, and $V_{ss}+$ provides an input to pin A of the timer 156. The output of the trigger 166 is the input to pin C of the timer 156. The coupled inputs of each trigger 154 and 166 are also connected through a normally open connection to $V_{dd}-$ and the 8-Bypass, Mono-in, Set and Clock Inhibit inputs of timer 156 and to the MOSFET source of the optocoupler 150, discussed previously. This normally open connection, when closed using a test jumper, provides inputs into the programmable timer 156, which enables a test mode.

As also shown in FIG. 5B, the Out 1 and Out 2 pins of the timer 156 are used in conjunction with the In-1 pin of the timer 156 to form an RC oscillator. Specifically, the Out 1 pin is connected to a capacitor, while the Out 2 pin is connected to a resistor. The capacitor and the resistor are commonly connected to another resistor connected to the In-1 pin. The Decode Out of the timer 156 provides an input to the Osc Inhibit pin, and also provides both inputs to a 2-input NAND Schmitt trigger 168, the output of which is connected to the power supply 12. Thus, this circuit provides an auto shut-down sequence.

FIG. 5B also shows the details of the power supply 12 of the apparatus 10. The power supply 12 is a standard design providing operating voltages of $V_{ss}+$ and $V_{dd}-$, and precision voltages of +DC volts and −DC volts. As mentioned in the discussion of FIG. 1, the power supply 12 preferably includes a single nine-volt battery 170. As shown in FIG. 5B, one terminal of the battery 170 is connected through a diode to $V_{ss}+$. The second terminal of the battery 170 is connected through second diode to $V_{ss}+$. Prior to its connection to the second diode, the second terminal of the battery 170 is connected to source of a power MOSFET 172 at a voltage of $V_{dd}-$. The source of the power MOSFET 172 is also connected to the low voltage input of the timer 156, the 8-Bypass, Mono-in, Set and Clock Inhibit inputs of timer 156 and the MOSFET source of the optocoupler 150, discussed previously. The power MOSFET 172 can be any standard n-channel power MOSFET, such as IRFD120 from Harris Semiconductor (Intersil Corporation) of Palm Bay, Fla.

As mentioned, the Decode Out of the timer 156 provides both inputs to a 2-input a NAND Schmitt trigger 168. The output of the trigger 168 is connected to the gate of the power MOSFET 172 through a resistor. The drain of the power MOSFET 172 is connected to the grounded common 174. The common 174 is also connected to the ground (Gnd.) of a power supply switcher 176. The switcher 176 is a switching regulator that supplies a fixed output of preferably 12 volts. One appropriate switcher 176 is the CMOS fixed/adjustable output step-up switching regulator MAX632 by Maxim Integrated Products of Sunnyvale, Calif.

The switcher 176 shown in FIG. 5B produces a regulated output, Vout. The positive output 178 of Vout is +12.0 volts since Vfb is grounded. Through the use of two external capacitors and diodes connected to the CP pin, a negative output 180 of 12.0 volts is also generated. A lead compensation capacitor is connected between the compensation input Comp and Vout. The low battery detector input LBi is connected to $V_{ss}+$ through a resistor and ground through another resistor, while the low battery detector output LBo is connected to an input of the digital panel meter 104 of the meter board 42, as shown in FIG. 4. In the switcher 176 shown in FIG. 5B, the Lx pin is connected through an external inductor to $V_{ss}+$.

The regulated 12 volt output of the switcher 176 is used to produce +DC volts and −DC volts. Specifically, the positive output 178 from Vout is connected to ground through a capacitor prior to being supplied to a first precision 5.0 volt shunt regulator diode 182 producing a precision voltage of −DC volts. Similarly, the negative output 180 is connected to ground through a capacitor prior to being supplied to a second precision 5.0 volt shunt regulator diode 184 producing a precision voltage of +DC volts. The output of each regulator diode 182, 184 is grounded through a capacitor. The shunt regulator diodes 182, 184 could each be LM320LZ-5.0 reference diodes from National Semiconductor Corp. of Santa Clara, Calif.

Thus, the present invention measures the resistance and reactance of a subject, or portion of a subject, while isolating the subject from the electronic components of the apparatus through the use of coupling transformers. Accuracy is achieved, in part, due the accuracy of the constant current system, which supplies a constant current within 1.0% of the targeted value. Accuracy is also assured by measuring the current at the subject across a reference resistor, not at the source, eliminating all phase shift between the source reference and the leads. Common mode rejection is inherent throughout the design and temperature drift is low, greatly reducing power consumption. Due to the low power consumption, a nine volt battery will last for a year under normal operations.

What is claimed is:

1. An apparatus for measuring an impedance of a segment of a subject, comprising:
   a constant current source wherein a level of an input current is controlled by a feedback loop using an error signal representing a difference between an actual current measured through the segment and a target current; and
   an impedance measuring circuit detecting an output voltage across the segment and adapted to produce at least one of a reactance output signal and a resistance output signal using the output voltage; and wherein neither one of the constant current source and the impedance measuring circuit share a common ground with the subject.

2. The apparatus according to claim 1, further comprising:
   reporting means for reporting at least one of the reactance output signal and the resistance output signal.

3. The apparatus according to claim 1, wherein the constant current source supplies the input current through first external leads connectable to the segment and the impedance measuring circuit measures the output voltage through second external leads connectable to the segment.

4. An apparatus for measuring an impedance of a segment of a subject, comprising:
   a constant current source wherein a level of an input current is controlled by a feedback loop using an error signal representing a difference between an actual current measured through the segment and a target current; and
   an impedance measuring circuit detecting an output voltage across the segment and adapted to produce at least one of a reactance output signal and a resistance output signal using the output voltage; and wherein the constant current source includes:
      a direct power supply providing a voltage source to an oscillating current source;
      a first amplifier connected to the oscillating current source wherein the gain of the first amplifier is controlled by the feedback loop; and
      an input coupling transformer receiving the output of the first amplifier and adapted to supply the input current through first external leads connectable to the segment.

5. The apparatus according to claim 4, wherein the oscillating current source comprises:
   a single field-effect transistor configured as a Colpitts oscillator.

6. An apparatus for measuring an impedance of a segment of a subject, comprising:
   a constant current source wherein a level of an input current is controlled by a feedback loop using an error signal representing a difference between an actual current measured through the segment and a target current; and
   an impedance measuring circuit detecting an output voltage across the segment and adapted to produce at least one of a reactance output signal and a resistance output signal using the output voltage; and wherein the feedback loop of the constant current source includes:
      a reference resistor coupled to a reference coupling transformer for measuring a constant current signal corresponding to the actual current through the segment;
      means for producing the error signal by comparing the constant current signal to a reference signal corresponding to the target current; and
      a modulator for controlling the gain of an amplifier of the constant current source using the error signal.

7. The apparatus according to claim 6, wherein the modulator is an optocoupler that changes resistance based on a value of the error signal.

8. The apparatus according to claim 6, wherein the means for producing the error signal comprises:
   a buffer amplifier connected to the reference transformer and adapted to produce an amplified constant current signal;
   a rectifier connected to the buffer amplifier and adapted to rectify the amplified constant current signal; and
   a comparator receiving an output of the rectifier and the reference signal and producing the error signal.

9. An apparatus for measuring an impedance of a segment of a subject, comprising:
   a constant current source wherein a level of an input current is controlled by a feedback loop using an error signal representing a difference between an actual current measured through the segment and a target current; and
   an impedance measuring circuit detecting an output voltage across the segment and adapted to produce at least one of a reactance output signal and a resistance output signal using the output voltage; and wherein the impedance measuring circuit comprises:
      a detection coupling transformer adapted to detect the output voltage;
      an output amplifier connected to the detection transformer adapted to produce an amplified output signal; and
      means for converting the amplified output signal into the at least one of the reactance output signal and the resistance output signal.

10. The apparatus according to claim 9, wherein the amplified output signal is capacitively coupled to the means for converting the amplified output signal into the reactance output signal and the resistance output signal.

11. The apparatus according to claim 9, wherein the detection coupling transformer is designed for a common mode rejection ratio of greater than 90 dB at its operating frequency.

12. The apparatus according to claim 9, wherein the feedback loop comprises:
    a reference resistor coupled to a reference transformer for measuring a constant current signal corresponding to the actual current through the segment; and
    a buffer amplifier connected to the reference transformer and adapted to produce an amplified constant current signal; and
    wherein the means for converting the output voltage into the reactance output signal and the resistance output signal includes:
       an integrator connected to receive the amplified constant current signal;
       a first balanced synchronous demodulator adapted to produce a first and a second direct current differential signal using a first reference vector provided by the integrator;
       a second balanced synchronous demodulator adapted to produce a third and a fourth direct current differential signal using a second reference vector provided by the buffer amplifier;

a first instrumentation amplifier adapted to convert the first and second direct current differential signals into the reactance output signal; and a second instrumentation amplifier adapted to convert the third and fourth direct current differential signals into the resistance output signal.

13. The apparatus according to claim 12, wherein the first and the second balanced synchronous demodulators are two passive analogue phase detectors.

14. An apparatus for measuring an impedance of a segment of a subject, comprising:

a constant current source wherein a level of an input current is controlled by a feedback loop using an error signal representing a difference between an actual current measured through the segment and a target current;

an impedance measuring circuit detecting an output voltage across the segment and adapted to produce at least one of a reactance output signal and a resistance output signal using the output voltage; and an automatic shut down circuit adapted to shut down operation of at least one of the constant current source and the impedance measuring circuit after at least one predetermined time period.

15. The apparatus according to claim 14, wherein the automatic shut down circuit comprises:

isolating means to isolate a power supply from at least one of the constant current source and the impedance measuring circuit.

16. An apparatus for measuring an impedance of a segment of a subject, comprising:

a constant current source supplying a level of an input current to an input coupling transformer through first external leads connectable to the segment;

a detection coupling transformer detecting an output voltage across the segment through second external leads connectable to the segment; and a circuit adapted to produce at least one output signal using the output voltage.

17. The apparatus according to claim 16, further comprising:

a reference resistor coupled to a reference coupling transformer for measuring a constant current signal corresponding to an actual current through the segment and providing an input to the constant current source.

18. The apparatus according to claim 16, wherein the level of the input current is controlled by an error signal representing a difference between an actual current measured through the segment and a target current.

19. The apparatus according to claim 18, further comprising:

an optocoupler controlling the level of the input current using the error signal.

20. The apparatus according to claim 16, wherein the detection coupling transformer is designed for a common mode rejection ratio of greater than 90 dB at its operating frequency.

* * * * *